United States Patent [19]

Seufert et al.

[11] Patent Number: 4,599,329

[45] Date of Patent: Jul. 8, 1986

[54] O,S-DIALKYL S-[CARBAMYLOXYALKYL] DITHIOPHOSPHATES AND THEIR USE AS PESTICIDES

[75] Inventors: Walter Seufert, Speyer; Hans-Peter Loeffler, Ludwigshafen; Ulrich Schirmer, Heidelberg; Wolfgang Seppelt, Bobenheim-Roxheim; Heinrich Adolphi, Limburgerhof, all of Fed. Rep. of Germany

[73] Assignee: BASF Aktiengesellschaft, Fed. Rep. of Germany

[21] Appl. No.: 570,456

[22] Filed: Jan. 13, 1984

[30] Foreign Application Priority Data

Jan. 22, 1983 [DE] Fed. Rep. of Germany ....... 3302095

[51] Int. Cl.$^4$ ..................... A01N 57/02; C07F 9/165
[52] U.S. Cl. ................................... 514/119; 558/107; 558/172
[58] Field of Search ................... 260/938; 514/119

[56] References Cited

U.S. PATENT DOCUMENTS 3,862,268  2/1973  Schrader et al. .................. 260/938
4,387,095  6/1983  Saito et al. ........................ 424/211

FOREIGN PATENT DOCUMENTS 791824  3/1958  United Kingdom .

*Primary Examiner*—Anton H. Sutto
*Attorney, Agent, or Firm*—Keil & Weinkauf

[57] ABSTRACT

O,S-dialkyl S-[carbamyloxyalkyl] dithiophosphates of the general formula (I)

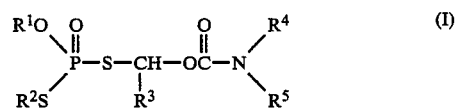

where, independently of one another, $R^1$ and $R^2$ are each alkyl of not more than 4 carbon atoms and $R^3$, $R^4$ and $R^5$ are each hydrogen or alkyl of not more than 6 carbon atoms, or $R^4$ and $R^5$, together with the nitrogen atom to which they are bonded, form a saturated or olefinically unsaturated ring which contains not more than 6 carbon atoms and may or may not contain one or more oxygen, sulfur or nitrogen atoms, are used for controlling insects or mites.

5 Claims, No Drawings

O,S-DIALKYL S-[CARBAMYLOXYALKYL] DITHIOPHOSPHATES AND THEIR USE AS PESTICIDES

It has been disclosed (cf. German Published Application DAS No. 1,060,659 and German Laid-Open Application DOS No. 2,206,678) that O,O-dialkyl S-[N-monoalkylcarbamyloxymethyl](thiono)thiophosphates and O-alkyl S-[carbamyloxymethyl](thiono)thiophosphates or -phosphenates, eg. O,O-diethyl S-[N-methylcarbamyloxymethyl]thiophosphate or O,O-diethyl S-[N-methylcarbamyloxymethyl]thionothiophosphate, have an insecticidal and acaricidal action.

We have found that novel O,S-dialkyl S-[carbamyloxyalkyl]dithiophosphates of the general formula (I)

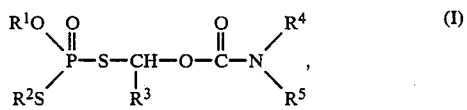

where, independently of one another, $R^1$ and $R^2$ each represent alkyl of not more than 4 carbon atoms and $R^3$, $R^4$ and $R^5$ each represent hydrogen or alkyl of not more than 6 carbon atoms, or $R^4$ and $R^5$, together with the nitrogen atom to which they are bonded, form a saturated or olefinically unsaturated ring which contains not more than 6 carbon atoms and may or may not contain one or more oxygen, sulfur or nitrogen atoms, have a substantially better insecticidal and acaricidal action than the conventional O,O-dialkyl S-[carbamyloxymethyl](thiono)thiophosphates having a similar constitution and the same type of action. The novel products hence constitute a genuine enrichment of the art.

The novel O,S-dialkyl S-[carbamyloxyalkyl]dithiophosphates (I) can be obtained if an appropriate O,S-dialkyl dithiophosphate of the general formula (II)

where M is an equivalent of an alkali metal, of an alkaline earth metal or of an unsubstituted or alkyl-substituted ammonium ion, is reacted with an appropriate monohaloalkyl carbamate of the formula (III)

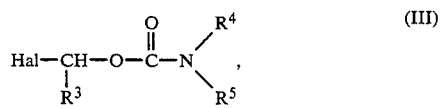

where Hal is chlorine or bromine.

If, for example, the dimethylammonium salt of O-ethyl S-n-propyldithiophosphoric acid and monochloromethyl N-methylcarbamate are used as starting materials, the course of the reaction can be represented by the following equation:

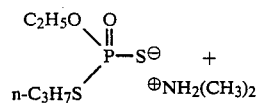

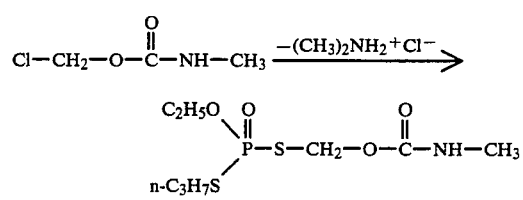

Formulae (II) and (III) give a general definition of the starting materials used. $R^1$ and $R^2$ are each preferably straight-chain or branched alkyl of 2 to 4 carbon atoms, eg. ethyl, n-propyl, isopropyl, sec.-butyl or isobutyl, $R^3$ is preferably hydrogen, methyl or ethyl, and $R^4$ and $R^5$ are each preferably methyl or ethyl, or $NR^4R^5$ is pyrrolidyl, piperidyl or morpholinyl.

Examples of phosphates (II) are the potassium, sodium and ammonium salts of O-methyl- or O-ethyl-S-ethyl or -n-propyl- or -isopropyl- or -isobutyl- or -sec.-butyldithiophosphoric acid.

Examples of carbamates (III) are monochloromethyl and monobromomethyl N-methyl-, N-ethyl-, N-propyl-, N-isopropyl-, N,N-tetramethylene-, N,N-dimethyl-, N,N-diethyl- or N,N-dipropylcarbamate.

The above starting materials can be obtained readily and in good yield, even on an industrial scale. They are obtained by, for example, chlorinating methyl chloroformate (cf. Hentschel, J. prakt. Chem. (2) 36, 213 [18877]) and then reacting the resulting monochloromethyl chloroformate with ammonia or an appropriate primary or secondary amine.

Virtually all inert organic solvents and diluents are suitable for carrying out the preparation process. These include, in particular, aliphatic and aromatic hydrocarbons and chlorohydrocarbons, eg. benzene, toluene, xylene, gasoline, methylene chloride, chloroform, carbon tetrachloride and chlorobenzene, ethers, eg. diethyl ether and dibutyl ether, ketones, eg. acetone, methyl ethyl ketone, methyl isopropyl ketone and methyl isobutyl ketone, and alcohols, eg. isopropanol, as well as other solvents. However, nitriles, eg. acetonitrile and propionitrile, have proven particularly useful.

The reactions take place in general at a sufficiently high temperature below 100° C., preferably at no higher than 70° C., under atmospheric pressure.

The compounds (II) and (III) are employed in general in stoichiometric amounts. An excess of one or other of the reactants has no substantial advantages, but may be employed in the reaction.

The novel compounds are generally obtained in the form of colorless or slightly yellow viscous water-insoluble oils; these cannot be distilled without decomposition, but can be freed from volatile components by incipient distillation, ie. prolonged heating at moderately elevated temperatures under reduced pressure, and can be purified in this manner. They are characterized, in particular, by their refractive index.

As stated above, the compounds according to the invention possess excellent insecticidal and acaricidal properties. They exhibit good activity both against sucking and biting insects, Diptera and mites, as well as a systemic and soil-insecticidal action; in particular, they have an excellent action against Lepidoptera. Moreover, these compounds are substantially less toxic than those described in German Laid-Open Application DOS No. 2,206,678.

PREPARATION EXAMPLES

Alpha-monochloroethyl N,N-dimethylcarbamate, which is used as an example of a starting material, was prepared as follows: 55 g (0.38 mole) of alpha-chloroethyl chloroformate were dissolved in 500 ml of ether, 38 g (0.4 mole) of condensed dimethylamine were slowly added dropwise at −30° C. and the mixture was left to stand overnight at room temperature. Dimethylammonium chloride was filtered off, and washed with ether, and the filtrate was evaporated down at room temperature under reduced pressure. The residue was distilled to give 32.5 g (0.215 mole) of alpha-monochloroethyl N,N-dimethylcarbamate of boiling point 40°–42° C./0.4–0.5 mbar.

Analysis (molecular weight 152): Calculated: C 39.6, H 6.7, N 9.2, Cl 23.4. Found: C 39.7, H 6.8, N 9.3, Cl 24.2.

EXAMPLE 1

O-Ethyl S-n-propyl S-[N,N-tetramethylenecarbamyloxymethyl]dithiophosphate 6.5 g (0.04 mole) of monochloromethyl N,N-tetramethylenecarbamate were gradually added to 12.3 g (0.05 mole) of dimethylammonium O-ethyl S-n-propyl dithiophosphate in 100 ml of acetonitrile at room temperature. After 4 hours at 50° C., the mixture was evaporated down under reduced pressure, the residue was taken up in 300 ml of toluene, and the solution was washed with three times 50 ml of water and dried over Na$_2$SO$_4$. After the major part of the solvent had been distilled off, the residue was left for a further 1.5 hours at 50° C. under reduced pressure from an oil pump. Yield: 8.5 g (0.026 mole), corresponding to 65% of theory; n$_D^{22}$=1.5229.

Analysis (based on a molecular weight of 327): Calculated: C 40.4, H 6.8, N 4.3, S 19.6, P 9.4. Found: C 40.6, H 6.7, N 4.5, S 18.9, P 8.7.

EXAMPLE 2

O-ethyl S-n-propyl S-[N,N-(3-oxa)-pentamethylenecarbamyloxymethyl]dithiophosphate 7.2 g (0.04 mole) of monochloromethyl N,N-(3-oxa)-pentamethylenecarbamate were added to 12.3 g (0.05 mole) of dimethylammonium O-ethyl S-n-propyl dithiophosphate in 100 ml of acetonitrile at room temperature. The mixture was heated at 50° C. for 4 hours, after which the solvent was removed under reduced pressure, the residue was taken up in 300 ml of toluene, and the solution was extracted by shaking with three times 50 ml of water and dried over Na$_2$SO$_4$. After the major part of the solvent had been distilled off, the residue was left for a further 2 hours under reduced pressure from an oil pump. Yield: 7.5 g (0.022 mole=55%) of a yellow oil; n$_D^{21}$=1.5240.

Analysis (molecular weight 343): Calculated: C 38.5, H 6.5, N 4.1. Found: C 38.7, H 6.5, N 4.4.

EXAMPLE 3

O-Ethyl S-i-propyl S-[N,N-dimethylcarbamyloxymethyl]dithiophosphate 5.6 g (0.04 mole) of monochloromethyl N,N-dimethylcarbamate were added to a stirred solution of 11.8 g (0.048 mole) of dimethylammonium O-ethyl S-i-propyl dithiophosphate in 100 ml of acetonitrile at room temperature. After 10 hours at 35° C., the solvent was stripped off under reduced pressure, the residue was taken up in 300 ml of toluene, the solution was washed rapidly with three times 50 ml of water and dried over Na$_2$SO$_4$. The major part of the solvent was distilled off under reduced pressure, and the remaining yellow oily ester was left for a further 2 hours at 50° C. under reduced pressure from an oil pump. Yield: 7.7 g (0.026 mole=65%); n$_D^{26}$=1.5085.

Analysis (molecular weight 301): Calculated: C 35.9, H 6.7, N 4.7, S 21.3, P 10.3. Found: C 35.6, H 6.6, N 4.9, S 21.5, P 10.1.

EXAMPLE 4

O-Ethyl S-sec.-butyl S-[N-methylcarbamyloxymethyl]dithiophosphate 4.9 g (0.04 mole) of monochloromethyl N-methylcarbamate were added to 13.0 g (0.05 mole) of dimethylammonium O-ethyl S-sec.-butyl dithiophosphate in 100 ml of acetonitrile at room temperature. After 2 hours at 50° C., the solvent was stripped off under reduced pressure, the residue was taken up in 300 ml of toluene, and the solution was washed rapidly with three times 50 ml of water, dried over Na$_2$SO$_4$ and evaporated down under reduced pressure. The remaining ester was left for a further 2 hours at 40° C. under reduced pressure from an oil pump. Yield: 7.5 g (0.025 mole=63%) of a yellow viscous oil; n$_D^{23}$=1.5165.

Analysis (molecular weight 301): Calculated: C 35.8, H 6.6, N 4.6, S 21.2, P 10.3. Found: C 35.8, H 6.6, N 4.5, S 21.7, P 10.4.

The compounds listed together with their refractive index in the Table below were obtained in similar yield, using appropriate modifications of the above preparation examples.

The remaining compounds can be obtained by appropriate use of other starting materials; because of their structural similarity, their action is expected to be similar to that of the compounds investigated in more detail.

TABLE $$\begin{array}{c} R^1O \quad O \qquad\qquad O \quad R^4 \\ \diagdown \| \qquad\qquad\qquad \| \diagup \\ P-S-CH-O-C-N \\ \diagup \qquad | \qquad\qquad \diagdown \\ R^2S \quad\; R^3 \qquad\qquad\;\; R^5 \end{array} \quad (I)$$

| Ex. no. | R$^1$ | R$^2$ | R$^3$ | R$^4$ | R$^5$ | °C. | n$_D$ |
|---|---|---|---|---|---|---|---|
| 5 | C$_2$H$_5$ | S—n-C$_3$H$_7$ | H | CH$_3$ | H | 26 | 1.5188 |
| 6 | " | S—i-C$_3$H$_7$ | " | " | " | 26 | 1.5160 |
| 7 | " | S—i-C$_4$H$_9$ | " | " | " | 23 | 1.5140 |
| 8 | " | S—sec.-C$_4$H$_9$ | " | " | CH$_3$ | 26 | 1.5060 |
| 9 | " | S—i-C$_4$H$_9$ | " | " | " | 23 | 1.5088 |
| 10 | " | S—n-C$_3$H$_7$ | CH$_3$ | " | " | 27 | 1.5015 |
| 11 | " | S—i-C$_3$H$_7$ | " | " | " | 27 | 1.5000 |
| 12 | " | S—sec.-C$_4$H$_9$ | H | —(CH$_2$)$_4$— | | 22 | 1.5200 |
| 13 | " | S—i-C$_4$H$_9$ | " | —(CH$_2$)$_4$— | | 22 | 1.5190 |
| 14 | " | S—sec.-C$_4$H$_9$ | " | —(CH$_2$)$_2$—O—(CH$_2$)$_2$— | | 22 | 1.5185 |
| 15 | " | S—i-C$_4$H$_9$ | " | —(CH$_2$)$_2$—O—(CH$_3$)$_2$— | | 22 | 1.5148 |
| 16 | " | S—n-C$_3$H$_7$ | H | H | H | | |
| 17 | " | S—i-C$_3$H$_7$ | " | " | " | | |
| 18 | " | S—i-C$_4$H$_9$ | " | " | " | | |
| 19 | " | S—sec.-C$_4$H$_9$ | " | " | " | | |
| 20 | " | S—n-C$_3$H$_7$ | CH$_3$ | " | " | | |
| 21 | " | S—i-C$_3$H$_7$ | " | " | " | | |
| 22 | " | S—i-C$_4$H$_9$ | " | " | " | | |
| 23 | " | S—sec.-C$_4$H$_9$ | " | " | " | | |
| 24 | CH$_3$ | S—n-C$_3$H$_7$ | H | CH$_3$ | CH$_3$ | | |
| 25 | " | " | " | " | H | | |
| 26 | C$_2$H$_5$ | S—n-C$_3$H$_7$ | " | —(CH$_2$)$_5$— | | | |
| 27 | " | S—i-C$_3$H$_7$ | " | " | | | |
| 28 | " | S—i-CH— | " | " | | | |
| 29 | " | S—sec.-C$_4$H$_9$ | " | " | | | |
| 30 | " | S—n-C$_3$H$_7$ | " | —(CH$_2$)$_2$—S—(CH$_2$)$_2$— | | | |
| 31 | " | S—i-C$_3$H$_7$ | " | " | | | |
| 32 | " | S—i-C$_4$H$_9$ | " | " | | | |

TABLE-continued $$\begin{array}{c}R^1O\quad O\qquad\qquad O\quad R^4\\ \diagdown\|\qquad\qquad\|\diagup\\ P-S-CH-O-C-N\\ \diagup\qquad |\qquad\qquad\diagdown\\ R^2S\qquad R^3\qquad\qquad R^5\end{array}\quad (I)$$

| Ex. no. | $R^1$ | $R^2$ | $R^3$ | $R^4$ | $R^5$ | °C. | $n_D$ |
|---|---|---|---|---|---|---|---|
| 33 | " | S—n-$C_3H_7$ | $CH_3$ | " | | | |
| 34 | " | S—sec.-$C_4H_7$ | " | " | | | |
| 35 | " | S—n-$C_3H_7$ | " | $C_2H_5$ | $C_2H_5$ | | |
| 36 | " | S—sec.-$C_4H_9$ | " | " | " | | |
| 37 | " | " | " | $C_3H_7$ | H | | |
| 38 | " | S—i-$C_4H_9$ | " | " | " | | |
| 39 | " | S—n-$C_3H_7$ | H | " | $C_3H_7$ | | |
| 40 | " | S—i-$C_3H_7$ | " | " | " | | |
| 41 | " | S—i-$C_4H_7$ | " | " | " | | |
| 42 | " | S—sec.-$C_7H_7$ | " | " | " | | |
| 43 | " | S—n-$C_3H_7$ | $CH_3$ | " | " | | |
| 44 | " | S—i-$C_4H_9$ | " | " | " | | |
| 45 | " | S—sec.-$C_4H_9$ | " | " | " | | |

The above, and other, active ingredients according to the invention are applied in the manner usual for phosphates. Details on formulation, application techniques and mode of action, and details of suitable mixture components for achieving synergistic and other advantageous actions are given for example in U.S. Pat. No. 4,320,122.

The following compounds—disclosed in German Laid-Open Application DE-OS No. 2,206,678—were used for comparison purposes:

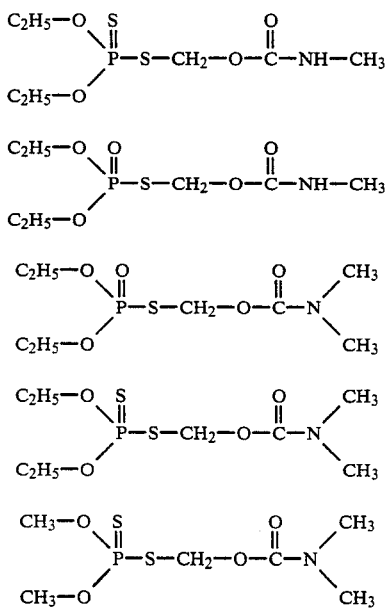

Breeding experiment with houseflies (*Musca domestica*)

4.5 ml of skimmed milk was introduced into 50 ml penicillin flasks, and 0.5 ml of the aqueous active ingredient formulation was then added. After brief mixing, a ball of absorbent cotton was introduced and about 50 housefly larvae placed on it. The flasks were covered and kept at room temperature. The development was assessed after 7 days.

In this experiment, the compounds of Examples 1, 2, 5, 7, 8, 9, 12, 13 and 14 were 100% effective at a concentration of from 0.2 to 0.5 ppm. The comparative agents were only effective at concentrations 10 times greater.

Contact action and effect of ingested food on caterpillars of the diamondback moth (*Plutella maculipennis*)

Leaves of young cabbage plants were dipped for 3 seconds in aqueous emulsions of the active ingredients and, after excess liquid had been briefly allowed to drip off, were placed on a moist filter paper in a Petri dish. 10 caterpillars of the 4th stage were then put on each leaf. The action was assessed after 48 hours.

In this experiment, the compounds of Examples 2, 4, 5, 8, 9, 12, 13, 14 and 15 were fully effective at a concentration of 0.005% or less, whereas the comparative agents A, B, C and D were only fully effective at a concentration 10 times higher.

Breeding experiment, Mediterranean fruit fly (*Ceratitis capitata*)

This experiment was carried out in 100 ml plastic beakers, using 40 g of a nutrient medium consisting of a 1:3 mixture of carrot powder and water, with added yeast.

The active ingredient was stirred as an aqueous formulation into the nutrient mix, which was then inoculated with 100 to 200 fresh eggs. The aqueous egg slurry had to be used very quickly to prevent the larvae hatching and dying.

The beakers were closed and kept at 24° to 26° C.; development was assessed after about a week.

In comparison to agent C, which was fully effective in a concentration of about 2 ppm, the compounds of Example 2, 4, 5, 6, 8, 9, 12, 13, 14 and 15 achieved a good action at concentrations up to 40 times less.

Action on caterpillars of *Agrotis ypsilon*

Young Indian corn leaves were dipped for 3 seconds in aqueous active ingredient formulations. After the layers had dried, the leaves were introduced into Petri dishes 12 cm in diameter and 5 caterpillars, each about 1.5 cm long, were placed on each leaf. The action was assessed after 48 hours.

In this experiment, concentrations of active ingredients 1, 5, 8, 12, 13 and 15 of less than 0.02% had a good action, whereas 4 of the comparative agents were still insufficiently effective at concentrations twice as high.

Contact action on ticks (*Ornithodorus moubata*)

The experiment was carried out on young ticks which had sucked blood only once. Commercially available tea-bags, each containing 5 animals, were dipped for 5 seconds in the aqueous active ingredient formulation.

The bags were then suspended. The temperature was kept at 25° to 26° C. The kill rate was determined after 48 hours.

In this test, all the active ingredients investigated were observed to have a good to full action at concentrations of as low as 10 ppm or less.

Action on root-knot nematodes (*Meloidogyne incognita*)

30 ml of aqueous formulations of the active ingredients was intimately mixed with 300 g of mold heavily infested with *Meloidogyne incognita*. The mold was then filled into plastic pots and tomato seedlings were planted therein. The pots were kept under greenhouse conditions at from 22° to 24° C.

The roots were checked for root-knots after 6 to 8 weeks.

In this experiment, root-knot formation was completely suppressed at an active ingredient concentration of 0.1% (and, in some instances, substantially less); the compounds investigated were nos. 4, 5, 7, 9, 12, 13, 14 and 15.

All the comparative compounds proved to be insufficiently active at a concentration of 0.1%.

We claim:

1. An O,S-dialkyl S-[carbamyloxyalkyl]-dithiophosphate of the formula

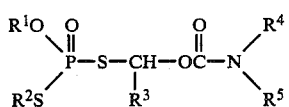 (I)

where, independently of one another, $R^1$ and $R^2$ each represent alkyl of not more than 4 carbon atoms and $R^3$, $R^4$ and $R^5$ each represent hydrogen or alkyl of not more than 6 carbon atoms, or $R^4$ and $R^5$, together with the nitrogen atom to which they are bonded, form a saturated or olefinically unsaturated ring which contains not more than 6 carbon atoms and may or may not contain one or more oxygen, sulfur or nitrogen atoms.

2. A process for combatting insects or mites which comprises: contacting the insects or mites or their habitat with an effective amount of a compound of the formula I as defined in claim 1.

3. An insecticidal and acaricidal composition comprising a carrier or diluent and an effective amount of a compound of the formula I as defined in claim 1.

4. A compound of the formula I of claim 1, wherein $R^3$ is hydrogen.

5. A compound of the formula I of claim 1, wherein $R^3$ is methyl.

* * * * *